United States Patent [19]

Morikawa et al.

[11] Patent Number: 5,663,543
[45] Date of Patent: Sep. 2, 1997

[54] METHOD FOR PRODUCING A POLYFLUOROPROPIONYL HALIDE

[75] Inventors: Shinsuke Morikawa; Hidekazu Okamoto; Keiichi Ohnishi; Toru Shimoyama; Naoko Wada; Yoshio Sato; Hideyuki Kurata, all of Yokohama, Japan

[73] Assignee: AG Technology Co., Ltd., Yokohama, Japan

[21] Appl. No.: 424,391

[22] PCT Filed: Aug. 31, 1994

[86] PCT No.: PCT/JP94/01434

§ 371 Date: May 1, 1995

§ 102(e) Date: May 1, 1995

[87] PCT Pub. No.: WO95/06629

PCT Pub. Date: Mar. 9, 1995

[30] Foreign Application Priority Data

Sep. 1, 1993 [JP] Japan ..................... 5-217212

[51] Int. Cl.$^6$ ..................... C07B 39/00
[52] U.S. Cl. ..................... 204/157.6; 204/157.87; 204/157.89; 204/157.94; 204/158.11
[58] Field of Search ..................... 204/157.6, 157.87, 204/157.89, 157.94, 158.11

[56] References Cited

U.S. PATENT DOCUMENTS

| | | | |
|---|---|---|---|
| 3,715,294 | 2/1973 | Browell et al. | 204/163 R |
| 3,883,407 | 5/1975 | Dittman et al. | 204/158 R |
| 4,004,572 | 1/1977 | Nathan et al. | 126/270 |
| 4,449,516 | 5/1984 | Kitao et al. | 126/430 |
| 5,259,938 | 11/1993 | Huang et al. | 204/157.87 |

*Primary Examiner*—Cecilia J. Tsang
*Assistant Examiner*—Cybille Delacroix-Muirheid
*Attorney, Agent, or Firm*—Oblon, Spivak, McClelland, Maier & Neustadt, P.C.

[57] ABSTRACT

A method for producing a polyfluoropropionyl halide, which is characterized by oxidizing at least one dichloropentafluoropropane selected from 3,3-dichloro-1,1,1,2,2-pentafluoropropane and 1,3-dichloro-1,1,2,2,3-pentafluoropropane by oxygen under irradiation with light and in the presence of chlorine.

The polyfluoropropionyl halide can be obtained from the dichloropentafluoropropane industrially advantageously in good yield. Further, in a gas phase reaction, the polyfluoropropionyl halide can be obtained in a very high reaction yield without decomposition of the desired product and without corrosion of the material for the reactor or the glass for the light source portion even in a reaction for a long period of time.

4 Claims, No Drawings

METHOD FOR PRODUCING A POLYFLUOROPROPIONYL HALIDE

TECHNICAL FIELD

The present invention relates to a method for producing a polyfluoropropionyl halide.

BACKGROUND ART

As methods for producing polyfluoropropionyl halides, (1) a method of oxidizing 1,1,1,3-tetrachlorotetrafluoropropane with fuming sulfuric acid in the presence of a halogen and under irradiation with light (Japanese Unexamined Patent Publication No. 237040/1985), and (2) a method by electrolytic fluorination of butyryl fluoride (U.S. Pat. No. 2,717,871) are, for example, known.

The method (1) can not be regarded as an industrial method, since a waste acid containing chlorine is formed in a large amount as a by-product. On the other hand, the method (2) can not be regarded as an economical method, since a large quantity of electric power is required, and a cost is required for separation from hydrogen gas formed as a by-product.

DISCLOSURE OF THE INVENTION

The present invention has been made to overcome the drawbacks of the conventional methods and is a method for producing a polyfluoropropionyl halide of the formula $RCF_2COX$ (wherein R is a $CF_3$ group or a $CClF_2$ group, and X is a Cl atom or a F atom), which is characterized by oxidizing at least one dichloropentafluoropropane (hereinafter referred to as R-225) selected from 3,3-dichloro-1,1,1,2,2-pentafluoropropane (hereinafter referred to simply as R-225ca) and 1,3-dichloro-1,1,2,2,3-pentafluoropropane (hereinafter referred to simply as R-225cb) by oxygen under irradiation with light and in the presence of chlorine.

The reaction of the present invention can be conducted in either a liquid phase or a gas phase. In the liquid phase reaction, it is preferred to employ a solvent having a high solubility of oxygen and chlorine to be present in the reaction system, for example, a perfluoro compound such as perfluorohexane, R-225ca or R-225cb.

The amount of the chlorine present is not particularly limited. However, if it is too small, the reaction rate decreases, and if it is too large, the by-product increases. Therefore, it is advisable to employ chlorine preferably in an amount of from 0.01 to 200 mols, more preferably from 0.3 to 200 mols, further preferably from 5 to 50 mols, per 100 mols of R-225. Such an amount of the chlorine present, may, of course, be varied to some extent depending upon various reaction conditions such as the temperature, the pressure or the reaction solvent.

The reaction temperature is not particularly limited so long as it is above the dew point of R-225 in the feed gas composition in the gas phase reaction. It is usually preferably within a range of from room temperature to 200° C., particularly within a range of from 50° to 150° C. In the liquid phase reaction, it is usually preferably within a range of from −50° to 100° C., particularly within a range of from −20° to 70° C.

The reaction pressure is not particularly limited in the gas phase reaction or in the liquid phase reaction, and the reaction readily proceeds under an optional pressure, for example, under atmospheric pressure. It of course depends upon other conditions such as the reaction temperature. For example, when the reaction is conducted in a liquid phase, it is preferred to conduct the reaction under a pressurized system in order to increase the dissolved amount of oxygen. Also in the gas phase reaction, it is preferred to conduct the reaction under a pressurized system in view of the reaction rate and the efficiency of the apparatus, so long as the temperature is above the dew point of R-225 in the feed gas composition, and the pressure is usually within a range of from atmospheric pressure to 5 kg/cm² (gauge), more preferably within a range of from atmospheric pressure to 3 kg/cm² (gauge). By increasing the amount of oxygen, the conversion of R-225 will usually increase.

The oxidation reaction by oxygen under irradiation with light according to the present invention can be carried out while diluting the oxygen preliminarily with a compound inert to the reaction intermediate or the reaction product, such as nitrogen, helium, argon or carbon dioxide. In a case where the reaction is conducted on an industrial scale, it is more preferred to dilute it with an inert gas such as nitrogen to make a reaction gas composition nonflammable whereby the explosion range of R-225 and oxygen, can be avoided.

Theoretically, oxygen is consumed in an amount of 50 mols per 100 mols of R-225. However, it may be employed in an amount of at least 50 mols, such as to a level of 400 mols, to increase the reaction rate of the dichloropentafluoropropane. To increase the selectivity for the polyfluoropropionyl halide, oxygen in an amount less than the theoretical amount, may be employed.

In the gas phase reaction, the supply molar ratio of R-225 and oxygen is preferably adjusted so that the proportion of oxygen is from 10 to 200 mols per 100 mols of R-225, preferably the proportion of oxygen is from 30 to 180 mols per 100 mols of R-225, more preferably the proportion of oxygen is from 50 to 150 mols per 100 mols of R-225, from the viewpoint of the reaction yield.

The light source to be used in the method of the present invention is not particularly limited, so long as it is capable of activating the chlorine present in the starting material or in the reaction system. For example, a high pressure mercury lamp, an intermediate pressure mercury lamp, a low pressure mercury lamp, a xenon lamp or a halogen lamp may be employed. If a proper light source is employed, the reaction may proceed without chlorine, however, it is not industrially advantageous, since the reaction rate tends to be slow as compared with the case where chlorine is present.

For photo-reaction, a method wherein irradiation with light is carried out through a reactor made of a fluorine resin and a method wherein irradiation with light is carried out by using a light source which is set in a reactor and protected against the reaction system by a covering outer cylinder equipped with a cooling means for cooling the light source, may be mentioned. In a photo-reaction involving production of hydrogen fluoride, even if hydrogen fluoride is produced even in a very small amount, a problem arises that the reaction rate decreases relatively early, since the hydrogen fluoride corrodes and devitrifies glass used for the outer cylinder for a light source which is directly in contact with the reaction atmosphere.

Therefore, it is preferred to form a protecting layer on an outer cylinder for a light source which comes into contact with the starting material and the reaction product of the oxidation reaction of the present invention. By avoiding direct contact between glass for the outer cylinder and the reactants, it is possible to prevent devitrification of glass, whereby the reaction can proceed smoothly for a long period of time.

The protecting layer is not particularly limited so long as it transmits effective light such as ultraviolet light emitted from the light source portion. For example, the protecting layer may be formed from a gas such as nitrogen or air. A resin which transmits ultraviolet light and is stable to ultraviolet light such as a fluorine resin, for example, a tetrafluoroethylene-perfluoroalkyl vinyl ether type polymer, tetrafluoroethylene-ethylene type copolymer, a tetrafluoroethylene-hexafluoropropylene type copolymer or a polymer having a fluorine-containing alicyclic structure, may be used as the protecting layer.

Formation of such a protecting layer makes it possible to avoid direct contact between by-products such as hydrogen fluoride and glass for the light source portion, and thereby prevented devitrification of glass. Therefore, the photo-oxidation reaction is allowed to continue for a long period of time.

U.S. Pat. No. 5,259,938 discloses a method for producing pentafluoropropionyl chloride, which is characterized by oxidizing R-225ca by oxygen in a liquid phase in the presence of chlorine and under irradiation with light having a wavelength longer than 280 nm.

In such a liquid phase reaction, corrosion of a metal material used for a reactor is remarkable, although its cause is not necessarily clear, and there is a problem that substantially no material can be used industrially for a reactor. Therefore, in the liquid phase reaction of the present invention, it is preferred to use the above-mentioned materials for a protecting layer as a material for a reactor.

Further, in the liquid phase reaction, since oxygen can dissolve in the reaction solution only in a low concentration, the amount of chlorine present in the reaction solution is preferably within a range of from 0.001 to 0.02M (mol/l), to inhibit formation of by-products due to chlorination reaction. However, in this case, the reaction yield of a polyfluoropropionyl halide becomes low. Accordingly, the reaction of the present invention is particularly preferred to be a gas phase reaction in the presence of chlorine, as described below.

In the gas phase reaction in the presence of chlorine of the present invention, since a sufficient reaction molar ratio of oxygen to R-225 is secured, the amount of trichloropentafluoropropane (hereinafter referred to as R-215), which is a by-product formed by chlorination, can be kept small, even if the chlorine concentration is high. Thereby, it is possible to make the chlorine concentration sufficiently high and to secure a high conversion of R-225.

The reaction product, a polyfluoropropionyl halide, shows its absorption wavelength in a range of from 250 nm to 280 nm, if in the reaction, the reaction system is irradiated with light having a short wavelength not more than 280 nm photolysis of the polyfluoropropionyl halide proceeds, whereby not only the selectivity for the desired product becomes low but also fluorine radical and hydrogen fluoride formed as by-products of the photolysis reaction corrode the glass of the outer cylinder for a light source.

Therefore, by conducting the reaction in a gas phase under selective irradiation with light having a wavelength longer than the decomposition wavelength of a polyfluoropropionyl halide, it is possible to obtain an effect that a polyfluoropropionyl halide can be produced stably on an industrial scale for a long period of time while the outer cylinder for the light source is prevented from corrosion due to hydrofluoric acid formed as a by-product in the photolysis.

The light having a wavelength longer than 280 nm to be used in the present invention is preferably in the absorption region of chlorine and its wavelength is selected preferably within a range of from 280 to 500 nm, more preferably within a range of from 280 to 450 nm. Although some types of light source emit light of a longer wavelength than this range, the light does not affect the reaction, and there is no need to specially cut light of a longer wavelength.

There are various methods for selective irradiation with light having a wavelength longer than 280 nm. For example, the following methods are preferable.

(1) A method wherein a light source which substantially hardly emits light having a wavelength not more than 280 nm such as a xenone lamp or a halogen lamp is employed. (2) A method wherein a light source which emits light including light having a wavelength 280 nm shorter is used while being covered with an outer cylinder made of a glass material which does not transmit light of a wavelength not more than 280 nm such as Pyrex (tradename, manufactured by Corning Company) so that light of a wavelength 280 nm or shorter is intercepted. (3) A method wherein a light source which emits light having a wavelength 280 nm or shorter is covered with an outer cylinder made of, for example, silica glass or a fluorine resin while a solution that absorbs light of a wavelength 280 nm or shorter is circulated in the outer cylinder as the cooling water of the light source, so that light having a wavelength not more than 280 nm is intercepted.

As the light source which emits light including light of wavelength 280 nm or shorter to be used in the above-mentioned methods (2) and (3), a high pressure, an intermediate pressure or a low pressure mercury lamp is preferable. As the solution to be used in the method (3), a copper sulfate aqueous solution, a potassium dichromate aqueous solution, a sodium silicate aqueous solution, a potassium iodide aqueous solution or a mixed solution thereof is preferable. A mixed solution of a potassium iodide aqueous solution with an alkali aqueous solution such as a sodium hydroxide aqueous solution is preferable.

A polyfluoropropionyl halide and polyfluoropropionic acid that can be easily obtained by conversion of a polyfluoropropionyl halide, are useful compounds used as various catalysts, intermediates of agricultural chemicals and medicines and intermediates of lubricating oils.

BEST MODE OF CARRYING OUT THE INVENTION

EXAMPLE 1

A vessel of 500 cc capacity made of a tetrafluoroethylene-perfluoroalkyl vinyl ether copolymer (hereinafter referred to as PFA) was immersed in a hot water bath at 80° C., and a mixed gas at 80° C. having a molar ratio of R-225ca, $O_2$ and $Cl_2$ of 5/4/1 was introduced at atmospheric pressure until the gas in the vessel was completely replaced. Then, the gas was irradiated with a 400 W high pressure mercury lamp outside the vessel for 10 minutes to carry out a gas phase reaction. After the reaction, the crude reaction gas was analyzed by $^{19}$F-NMR and by gas chromatography. As a result, the conversion of R-225ca was 99%, and the selectivity for pentafluoropropionyl chloride was 99%.

EXAMPLE 2

A gas phase reaction was conducted in the same manner as in Example 1 except that R-225cb was used instead of R-225ca. The reaction gas was analyzed by $^{19}$F-NMR and by gas chromatography. As a result, the conversion of R-225cb was 98%, and the selectivity for 3-chloro-1,1,2,2-tetrafluoropropionyl fluoride was 99%.

EXAMPLE 3

Into a PFA tubular reactor of 30 cc capacity which was set in a bath of 80° C., a reaction gas having been prepared so that the molar ratio of R-225ca, $O_2$ and $Cl_2$ would be 2/6/1 was introduced until the internal pressure of the reaction tube was kept at 2 kg/cm$^2$ (gauge pressure). Then, it was irradiated with a 400 W high pressure mercury lamp for 5 minutes outside the reactor to carry out a gas phase reaction. After the reaction, the crude reaction gas was analyzed by $^{19}$F-NMR and by gas chromatography. As a result, the conversion of R-225ca was 99%, and the selectivity for pentafluoropropionyl chloride was 99%.

EXAMPLE 4

A gas phase reaction was conducted in the same manner as in Example 3 except that a reaction gas having been prepared so that the molar ratio of R-225ca, $O_2$, $Cl_2$ and $N_2$ would be 1/1.4/0.5/1.6. After the reaction, the crude reaction gas was analyzed by $^{19}$F-NMR and by gas chromatography. As a result, the conversion of R-225ca was 99%, and the selectivity for pentafluoropropionyl chloride was 99%.

EXAMPLE 5

Into a 1,000 ml Hastelloy-C reactor with a condenser cooled at −80° C., 1.5 kg of R-225ca was charged, and then $Cl_2$ and $O_2$ were introduced into it at 0.5 mol/hr and at 2.0 mol/hr, respectively, while it was irradiated with a 400 W high pressure mercury lamp with a glass outer cylinder that was coated with a transparent fluorine resin CYTOP (tradename: a polymer having a fluorine-containing alicyclic structure, manufactured by Asahi Glass Company Ltd.), to conduct a liquid phase reaction at a reaction temperature of 0° C. After 6 hours of the reaction, the crude reaction product was analyzed by $^{19}$F-NMR and by gas chromatography. As a result, the conversion of R-225ca was 40%, and the selectivity for pentafluoropropionyl chloride was 95%.

EXAMPLE 6

A 2 kW high pressure mercury lamp equipped with a glass outer cylinder that was coated with a transparent fluorine resin CYTOP was set in a 100 l Hastelloy-C autoclave, and R-225ca, $O_2$, $Cl_2$ and $N_2$ were continuously fed at 2.47 mol/hr, 63 l/hr, 0.5 mol/hr and 117 l/hr, respectively, at atmospheric pressure under irradiation with light, while the internal temperature of the reactor was kept at 80° C. to 100° C., to conduct a gas phase reaction. The crude reaction gas withdrawn continuously from the outlet of the reactor was analyzed by $^{19}$F-NMR and by gas chromatography. As a result, the conversion of R-225ca was 95%, and the selectivity for pentafluoropropionyl chloride was 98%.

EXAMPLE 7

A reaction was conducted in the same manner as in Example 6 except that R-225 cb was used instead of R-225ca. The crude reaction gas was analyzed by $^{19}$F-NMR and by gas chromatography. As a result, the conversion of R-225cb was 92%, and the selectivity for 3-chloro-1,1,2,2-tetrafluoropropionyl fluoride was 96%.

EXAMPLE 8

Irradiation with a 1,000 W high pressure mercury lamp was conducted for 180 minutes in the same manner as in Example 1 except that a mixed gas warmed at 80° C. and having been prepared so that the molar ratio of R-225ca and $O_2$ would be 50/50 was used. After the reaction, the crude reaction gas was analyzed by $^{19}$F-NMR and by gas chromatography. As a result, the conversion of R-225ca was 70%, and the selectivity for pentafluoropropionyl chloride was 92%.

EXAMPLE 9

A 1 kW high pressure mercury lamp equipped with Pyrex outer cylinder was set in a 10 l Hastelloy-C reactor, and R-225ca, $Cl_2$, $O_2$ and $N_2$ were continuously fed from the bottom of the reactor at 0.51 mol/hr, 0.051 mol/hr, 0.20 Nl/min and 0.36 Nl/min, respectively, under irradiation with light, while the internal temperature of the reactor was kept at 80° C., to conduct a gas phase reaction (average retention time 10 min). The crude reaction gas continuously effused from the top of the reactor was analyzed by gas chromatography and by $^{19}$F-NMR, one hour after the reaction was started.

As a result, the conversion of R-225ca was 99%, the selectivity for pentafluoropropionyl chloride was 98%, and the selectivity for $CF_3CF_2CCl_3$ (hereinafter referred to as R-215cb) was 2%.

In the reaction system, test pieces made of SUS-316 and of Pyrex glass were placed, and the rates of corrosion were determined in terms of their weight losses after 300 hours of continuous reaction. The results are shown in Table 1.

EXAMPLE 10

Reaction and analysis were conducted in the same manner as in Example 9 except that R-225cb was used instead of R-225ca.

As a result, the conversion of R-225cb was 85%, the selectivity for 3-chloro-1,1,2,2-tetrafluoropropionyl fluoride was 96%, and the selectivity for $CClF_2CF_2CCl_2F$ (hereinafter referred to as R-215ca) was 4%.

EXAMPLE 11

A solution was prepared by dissolving potassium dichromate ($K_2CrO_4$) potassium iodide in a 0.1 wt % sodium hydroxide aqueous solution in concentrations of 0.1 g/l and 0.155 g/l, respectively, then it was circulated in an outer cylinder for a light source as a cooling water of a light source. Into a photo-reactor of 200 l capacity made of SUS-316 equipped with a light source portion having a 20 kW high pressure mercury lamp made of silica glass and an outer cylinder made of silica glass, R-225ca, $Cl_2$, $O_2$ and $N_2$ were continuously fed from the bottom of the reactor at flow rates of 460 Nl/hr, 44 Nl/hr, 420 Nl/hr and 960 Nl/hr, respectively, under irradiation of light through the outer cylinder, while the internal temperature of the reactor was kept at 65° C., to conduct a gas phase reaction, (average retention time 4.2 minutes).

One hour after the beginning of the reaction, the crude reaction gas continuously effused from the top of the reactor was analyzed by gas chromatography and by $^{19}$F-NMR. As a result, the conversion of R-225ca was 76%, the selectivity for pentafluoropropionyl chloride was 99.5%, and the selectivity for R-215cb was 0.5%. Even after the reaction was conducted continuously for 720 hours, neither corrosion nor erosion due to hydrofluoric acid was observed on the glass outer cylinder for the light source.

EXAMPLE 12

A 1 kW high pressure mercury lamp having a Pyrex outer cylinder was set in a 10 l Hastelloy-C reactor with a reflux condenser cooled at −50° C., and 1,200 g of R-225ca was charged to the reactor. Then, $Cl_2$ and $O_2$ were continuously fed from the bottom of the reactor at flow rates of 0.052 mol/hr and 0.45 mol/hr, respectively, while the internal temperature was cooled at 10° C. and irradiation with light was conducted, to conduct the reaction in a liquid phase. After 30 hours of the reaction, the composition of the reaction solution was analyzed by gas chromatography and $^{19}F$-NMR.

As a result, the conversion of R-225ca was 23%, the selectivity for pentafluoropropionyl chloride was 97%, the selectivity for R-215cb was 1%, and the selectivity for $CF_3CF_2CCl_2CCl_2CF_2CF_3$ was 2%. In the reaction system, test pieces made of various metals shown in Table 2 were placed, and the rates of corrosion were determined in terms of their weight losses during the reaction. The results are shown in Table 2.

EXAMPLE 13

Reaction was conducted in the same manner as in Example 11 except that pure water was circulated instead of the solution filter used in Example 11. The conversion of R-225ca was 98%, the selectivity for pentafluoropropionyl chloride was 33%, the selectivity for R-215cb was 38%, the selectivity for $CF_3CF_2CCl_2CCl_2CF_2CF_3$ was 18%, and the selectivity for others ($COF_2$, $COCl_2$, $CF_3CF_2Cl$, $CF_3CF_2CCl_2F$, etc.) was 11%.

After the reaction was continuously conducted for 100 hours, the glass outer cylinder for the light source was observed, to be corroded remarkably by hydrogen fluoride. In some extremely corroded portions, the glass was thinned to less than half.

TABLE 1

| Material | Rate of corrosion (mm/year) | Appearance |
|---|---|---|
| SUS-316 | 0.012 | Nothing unusual |
| Pyrex | 0.008 | Nothing unusual |

TABLE 2

| Material | Rate of corrosion (mm/year) | Appearance |
|---|---|---|
| Inconel | 0.432 | Rust, Orange peel |
| SUS-310S | 1.75 | Rust, Orange peel |
| SUS-316L | 3.72 | Rust, Orange peel |

TABLE 2-continued

| Material | Rate of corrosion (mm/year) | Appearance |
|---|---|---|
| Nickel | 0.33 | Rust, Orange peel |
| Monel | 0.42 | Rust, Orange peel |
| Hastelloy-C | 1.35 | Rust, Orange peel |
| Pyrex | 1.97 | Corrosion |

INDUSTRIAL APPLICABILITY

The polyfluoropropionyl halide can be obtained from the dichloropentafluoropropane industrially advantageously in good yield. Further, in a gas phase reaction, the polyfluoropropionyl halide can be obtained in a very high reaction yield without decomposition of the desired product and without corrosion of the material for the reactor or the glass for the light source portion even in a reaction for a long period of time.

We claim:

1. A method for producing a polyfluoropropionyl halide of the formula $RCF_2COX$, wherein R is a $CF_3$ group or a $CClF_2$ group, and X is a Cl atom or a F atom, which comprises oxidizing in a gas phase at least one dichloropentafluoropropane selected from the group consisting of 3,3-dichloro-1,1,2,2-pentafluoropropane and 1,3-dichloro-1,1,2,2-pentafluoropropane by oxygen under irradiation with light having a wavelength longer than 280 nm and wherein chlorine is present during the reaction, wherein the irradiation with light having a wavelength longer than 280 nm is carried out by emitting light from a light source covered with an outer cylinder while a solution that absorbs light of wavelength 280 nm or shorter is circulated in the outer cylinder to cool said light source, and wherein a fluorine resin protecting layer is formed on the outer cylinder.

2. The method according to claim 1, wherein the amount of the chlorine present is from 0.01 to 200 mols per 100 mols of the dichloropentafluoropropane.

3. The method according to claim 1, wherein the amount of the chlorine present is from 0.3 to 200 mols per 100 mols of the dichloropentafluoropropane, and the supply molar ratio of the dichloropentafluoropropane and the oxygen is such that the proportion of the oxygen is from 10 to 200 mols per 100 mols of the dichloropentafluoropropane.

4. The method according to claim 3, wherein the outer cylinder is made of a glass material which does not transmit light of wavelength 280 nm or shorter.

* * * * *